United States Patent
Dau et al.

(10) Patent No.: US 10,300,333 B2
(45) Date of Patent: May 28, 2019

(54) TECHNIQUES FOR EVALUATING SWING METRICS

(71) Applicant: Under Armour, Inc., Baltimore, MD (US)

(72) Inventors: Nathan Dau, Baltimore, MD (US);
Angela Nelligan, Baltimore, MD (US);
F. Grant Kovach, Baltimore, MD (US);
Mark A. Oleson, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

(21) Appl. No.: 15/607,805

(22) Filed: May 30, 2017

(65) Prior Publication Data
US 2018/0345075 A1 Dec. 6, 2018

(51) Int. Cl.
| | |
|---|---|
| A63B 69/36 | (2006.01) |
| A63B 24/00 | (2006.01) |
| H04W 4/80 | (2018.01) |
| H04L 29/08 | (2006.01) |
| G09B 19/00 | (2006.01) |
| H04W 4/02 | (2018.01) |

(52) U.S. Cl.
CPC ...... *A63B 24/0006* (2013.01); *A63B 69/3632* (2013.01); *H04L 67/12* (2013.01); *H04L 67/36* (2013.01); *H04W 4/80* (2018.02); *A63B 2220/34* (2013.01); *A63B 2225/50* (2013.01); *G09B 19/0038* (2013.01); *H04W 4/027* (2013.01)

(58) Field of Classification Search
USPC ....... 473/131, 150, 199, 220, 221, 222, 223, 473/409
See application file for complete search history.

(56) References Cited

U.S. PATENT DOCUMENTS

| | | | | |
|---|---|---|---|---|
| 5,638,300 | A * | 6/1997 | Johnson | A63B 24/0003 473/223 |
| 5,826,578 | A * | 10/1998 | Curchod | A61B 5/1121 434/252 |
| 6,148,280 | A * | 11/2000 | Kramer | A63B 69/3608 340/524 |
| 7,602,301 | B1 * | 10/2009 | Stirling | A61B 5/1127 340/573.1 |
| 8,414,411 | B2 * | 4/2013 | Stites | A63B 69/3614 473/221 |
| 9,046,919 | B2 * | 6/2015 | Niknejad | G06F 3/011 |
| 2004/0209698 | A1 * | 10/2004 | Ueda | A63B 24/0003 473/150 |
| 2005/0215336 | A1 * | 9/2005 | Ueda | A63B 24/0003 473/131 |
| 2010/0015585 | A1 * | 1/2010 | Baker | A63B 24/0003 434/247 |
| 2010/0151957 | A1 * | 6/2010 | Hohla | A63B 24/0003 473/221 |

(Continued)

*Primary Examiner* — Nini Legesse

(57) ABSTRACT

A shoe pod includes a positioning component and an altimeter. The positioning component determines geodetic locations of the shoe, whereas the altimeter determines elevations of the shoe. A golf club pod is disposed at the golf club and includes a golf club parameter detector operable to be detachably fastened to the golf club, to detect a golf club head striking surface position and to transmit the detected club parameter signal based on the detected golf club parameter.

13 Claims, 10 Drawing Sheets

(56) References Cited

U.S. PATENT DOCUMENTS

| | | | |
|---|---|---|---|
| 2010/0216565 A1* | 8/2010 | Stites | A63B 69/3614 |
| | | | 473/231 |
| 2010/0267462 A1* | 10/2010 | Mooney | A63B 69/36 |
| | | | 473/269 |
| 2013/0316840 A1* | 11/2013 | Marks | G09B 19/0038 |
| | | | 473/199 |

* cited by examiner

TECHNIQUES FOR EVALUATING SWING METRICS

BACKGROUND

The present invention generally relates to systems and method for monitoring golf swing techniques.

There exists a need for a system and method to effectively monitor a golf swing.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Overview

A system includes a shoe pod and a golf club pod. The shoe pod is disposed at the shoe and includes a positioning component and an altimeter. The positioning component determines a first geodetic location of the shoe at a first time, whereas the altimeter determines a first elevation of the shoe at the first time. The first positioning component additionally determines a second geodetic location of the shoe at a second time and generates shoe distance data based on the first geodetic location and the second geodetic location. The altimeter additionally determines a second elevation of the shoe at the second time. The positioning component additionally determines a total distance traveled based on the first shoe distance data, the first elevation and the second elevation. The golf club pod is disposed at the golf club and includes a golf club parameter detector operable to be detachably fastened to the golf club, to detect a golf club head striking surface position and to transmit the detected club parameter signal based on the detected golf club parameter.

Example Embodiments

Training devices have been in use in the golf industry to analyze a golf swing for a long time and, oftentimes, are very expensive to install or use, such as numerous cameras for viewing and other physical training devices to develop muscle memory. Viewing the user's golf swing on a camera or conditioning the muscle memory via training devices leads to a level of ambiguity, which may not provide the full potential intended by the device(s).

Currently, enhanced parameter detection and sensor technology has allowed an easier, more accurate, and less expensive manner to observe a golf swing. Using these parameter detectors in the golf shoes and golf club head allows the user the ability to determine certain parameters that can be observed in real time or stored and observed at a later time. Non-limiting detected parameters are: shoe position, golf club head position, or any combination of these components throughout the entire swing.

In accordance with aspects of the present invention, shoe detectors and golf club detector are detachably affixed to the shoes and golf club head. During the golf swing the shoes and golf club head parameters are detected and sent to a computer, smartphone, or other external device for real-time viewing or stored for later viewing. Observation of the results by the user or a trainer can allow the user to alter one or more parameters to create a better performance of the golf swing.

Aspects of the present invention will now be described with reference to FIGS. 1-12.

An overall system view example of the present invention will be described with reference to FIG. 1.

Figure 1:
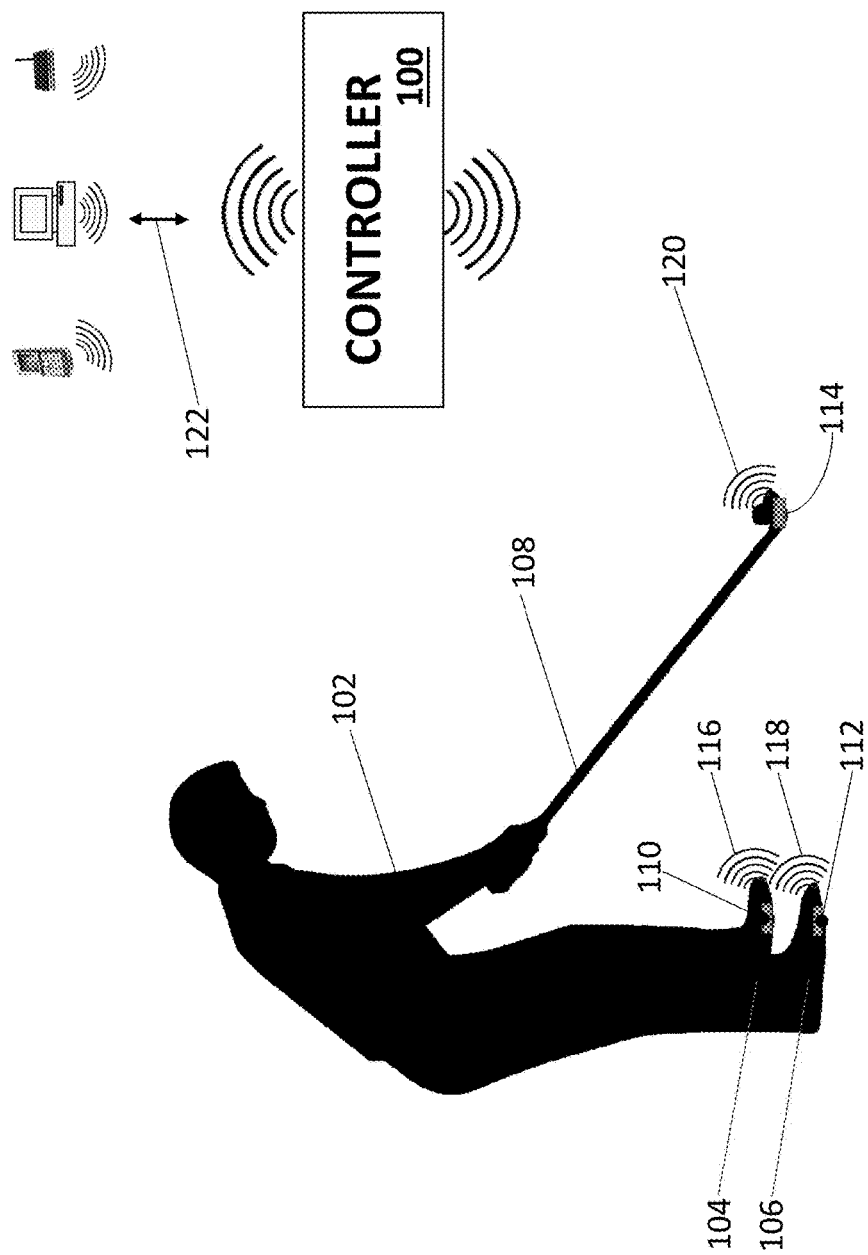
FIG. 1 illustrates a system for monitoring a golf swing in accordance with aspects of the present invention.

FIG. 1 illustrates a system for monitoring golf in accordance with aspects of the present invention.

FIG. 1 includes a controller 100, a user 102, a shoe 104, a shoe 106, a golf club 108, a shoe parameter detector 110, a shoe parameter detector 112, and a golf club parameter detector 114.

As shown in the figure, user 102 is holding golf club 108, which has the golf club parameter detector 114 positioned on the golf club. User 102 is wearing shoes 104 and 106, which house the shoe parameter detectors 110 and 112, respectively. Controller 100 communicates with golf club parameter detector 114, shoe parameter detector 110, shoe parameter detector 112, and external devices, e.g., smartphones and computers.

Shoe parameter detector 110 and shoe parameter detector 112 may be any device or system that can detect shoe parameters and send shoe parameter signals 116 and 118 based on the detected shoe parameters. Non-limiting examples of shoe parameters that may be detected by shoe parameter detectors 110 and 112 include: position, elevation, orientation, pressure, force, velocity, acceleration, change in elevation, change in orientation, change in pressure, change in force, change in acceleration and combinations thereof.

In some embodiments, each of shoe parameter detector 110 and shoe parameter detector 112 may detect an amplitude of a parameter at an instant of time. In some embodiments, each of shoe parameter detector 110 and shoe parameter detector 112 may detect a parameter vector at an instant of time. In some embodiments, each of shoe parameter detector 110 and shoe parameter detector 112 may detect an amplitude of a parameter as a function over a period of time. In some embodiments, each of shoe parameter detector 110 and shoe parameter detector 112 may detect a parameter vector as a function over a period of time. In some embodiments, each of shoe parameter detector 110 and shoe parameter detector 112 may detect a change in the amplitude of a parameter as a function over a period of time. In some embodiments, each of shoe parameter detector 110 and shoe parameter detector 112 may detect a change in a parameter vector as a function over a period of time.

Golf club parameter detector 114 may be any device or system that can detect a golf club parameter and send a detected golf club parameter signal 120 based on the detected golf club parameter. Non-limiting examples of golf club parameters that may be detected by golf club parameter detector 114 include: a position of a ball-striking surface of the club head relative to a position of shoe 104 or a position of shoe 106; elevation of the ball-striking surface of the club head relative to a position of shoe 104, orientation of the ball-striking surface of the club head relative a position of shoe 104 and a position of shoe 106; force of the ball-striking surface of the club head; velocity of the ball-striking surface of the club head; acceleration of the ball-striking surface of the club head; change in elevation of the ball-striking surface of the club head; change in orientation of the ball-striking surface of the club head; change in force of the ball-striking surface of the club head; change in acceleration of the ball-striking surface of the club head and combinations thereof.

Controller 100 receives detected shoe parameter signals from shoe parameter detectors 110 and 112, via shoe parameter signals 116 and 118, and controller 100 receives signals from golf club parameter detector 114 via golf club parameter signal 120. Controller 100 then sends a performance signal 122 to external devices, e.g., smartphones and computers. In other example embodiments, controller 100 is able to receive and hold the individual detected signals from each detecting component, wherein controller 100 is able to generate a performance signal as a composite detected signal that is based on the individual detected signals. The composite detected signal may be based on any of the individual detected signal, and combinations thereof. In some embodiments, controller 100 may additionally process any of the individual detected signals and combinations thereof to generate the composite detected signal. Non-limiting examples of further processes include averaging, adding, subtracting and transforming any of the individual detected signals and combinations thereof.

FIG. 1 is an overall example embodiment of the present invention showing the entire system view. The shoe parameter detectors and golf club parameter detector send individual signals to controller 100 which then sends a composite of these individual signals to external devices to show the performance of user 102.

Figure 2:
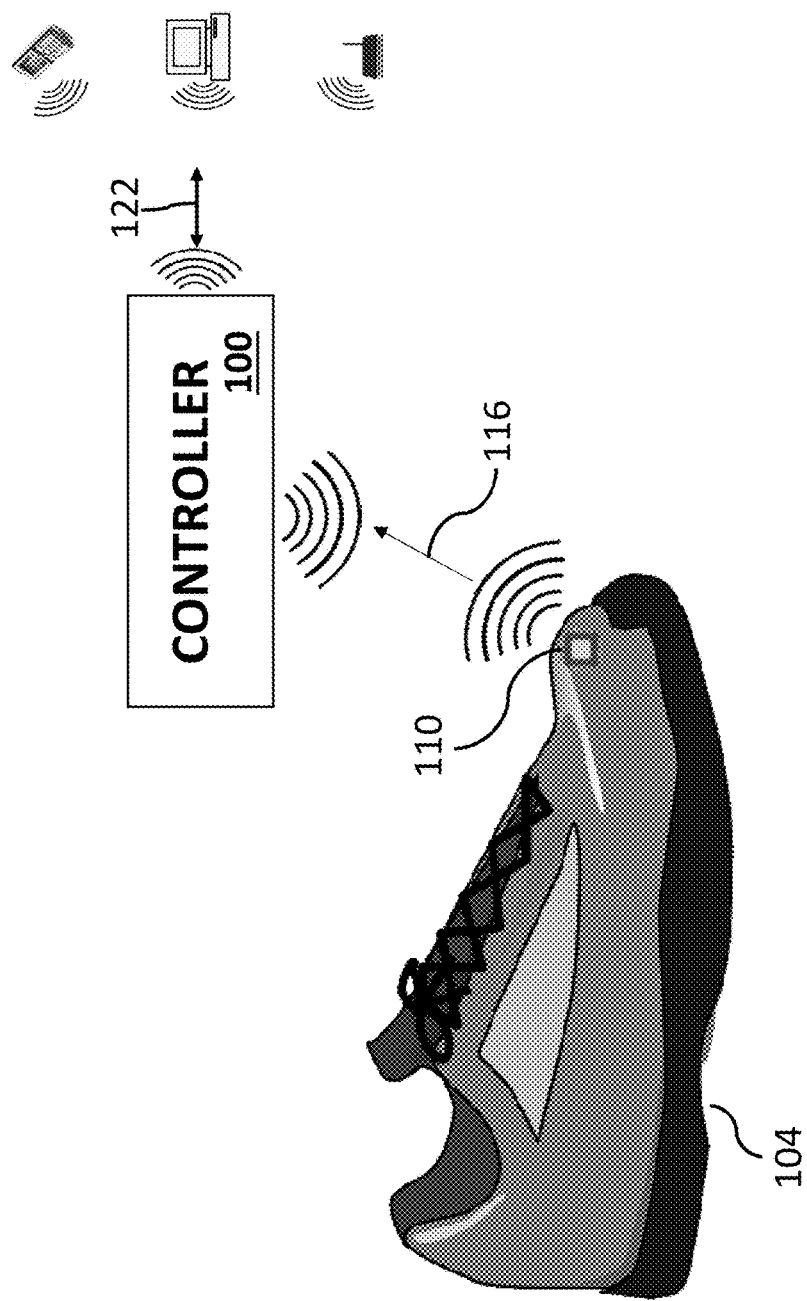
FIG. 2 illustrates a shoe parameter detection system in accordance with aspects of the present invention.

The specifics of shoe 104 will now be further described with additional reference to FIG. 2.

FIG. 2 includes shoe 104, shoe parameter detector 110 and a controller 100.

As shown in the figure, shoe parameter detector 110 is disposed at shoe 104. In some embodiments, shoe parameter detector 110 is disposed in shoe 104. In some embodiments, shoe parameter detector 110 is disposed on shoe 104. In some embodiments, shoe parameter detector 110 is detachably fastened to shoe 104. Controller 100 is located externally to shoe 104 and communicates with shoe parameter detector 110 and external devices, i.e., smartphones, computers, etc.

Shoe parameter detector 110 detects shoe parameters and sends detected shoe parameter signals to controller 100 based on the detected shoe parameters. Controller 100 sends detected shoe parameter (along with shoe parameter detector 112 signal and golf club parameter detector 114 signal) via a composite performance signal 122 to external devices, e.g., smartphones, computers, etc.

Figure 3:
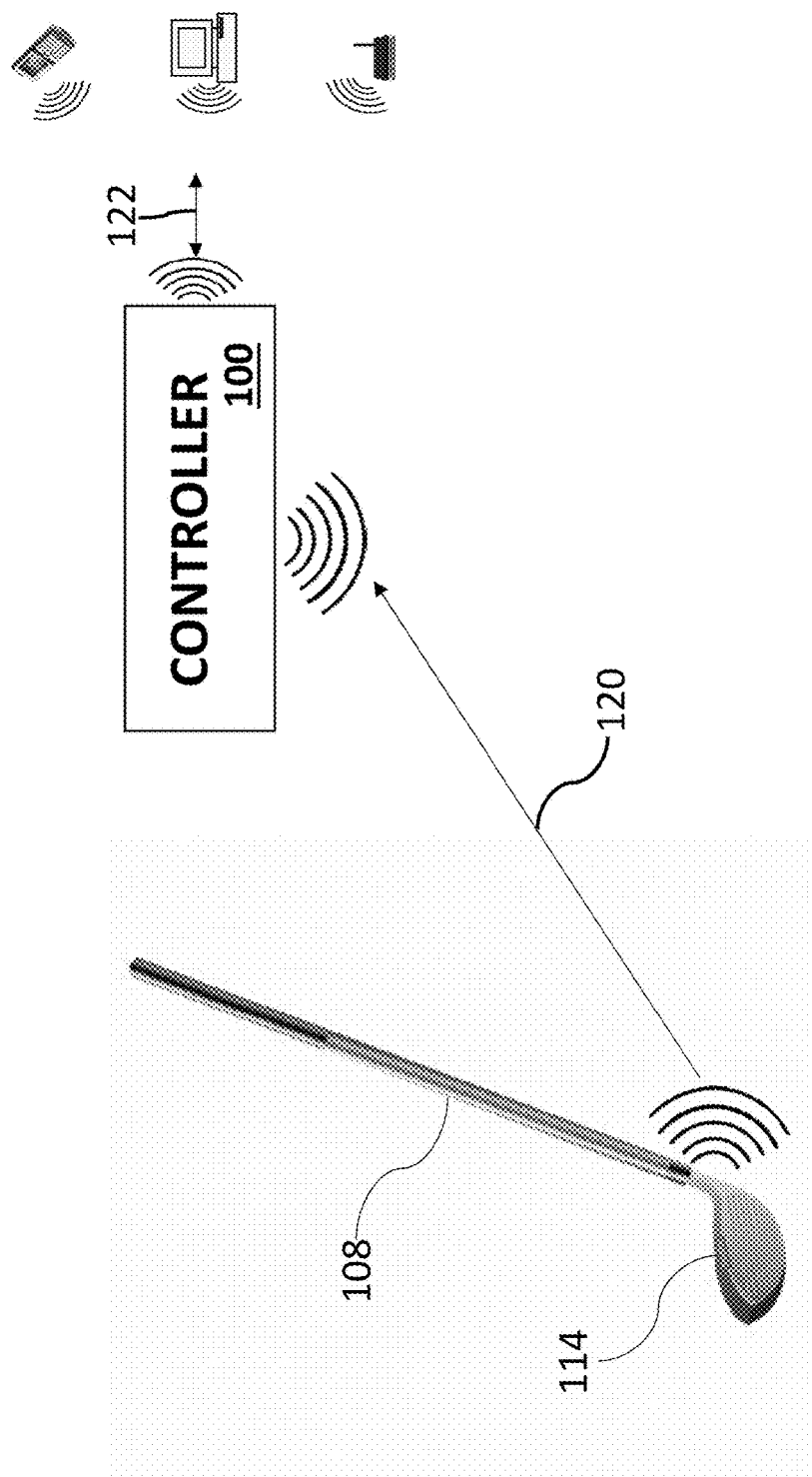
FIG. 3 illustrates a golf club parameter detection system in accordance with aspects of the present invention.

The specifics of golf club parameter detector 114 on golf club 108 will now be further described with additional reference to FIG. 3.

FIG. 3 includes golf club 108, golf club parameter detector 114 and controller 100.

As shown in the figure, golf club parameter detector 114 is disposed at golf club 108. In some embodiments, golf club parameter detector 114 is disposed on golf club 108. In some embodiments, golf club parameter detector 114 is detachably fastened to golf club 108. Controller 100 communicates with golf club parameter detector 114 and external devices, e.g., smartphones, computers, etc . . . via performance signal 122.

Golf club parameter detector 114 detects golf club parameters and sends detected golf club parameters to controller 100 based on the detected golf club parameters. Controller 100 sends detected golf club parameters (along with shoe parameter detector 110 signal and shoe parameter detector 112 signal) a composite performance signal 122 to external devices, e.g., smartphones, computers, etc . . . to show the performance of user 102. As stated previously, an object of a system in accordance with the aspects of the present invention is to track parameters of shoes and a golf club in order to track performance of play of the user. For example, the shoes may detect a plurality of different parameters; non-limiting examples of which include the position, orientation, pressure, or acceleration of each shoe during a swing, whereas a club may detect parameters such as acceleration, force, and velocity during a swing. These detected parameters may be stored and analyzed to analyze overall play of the user. This will be further described with reference to FIGS. 4-10.

Figure 4:
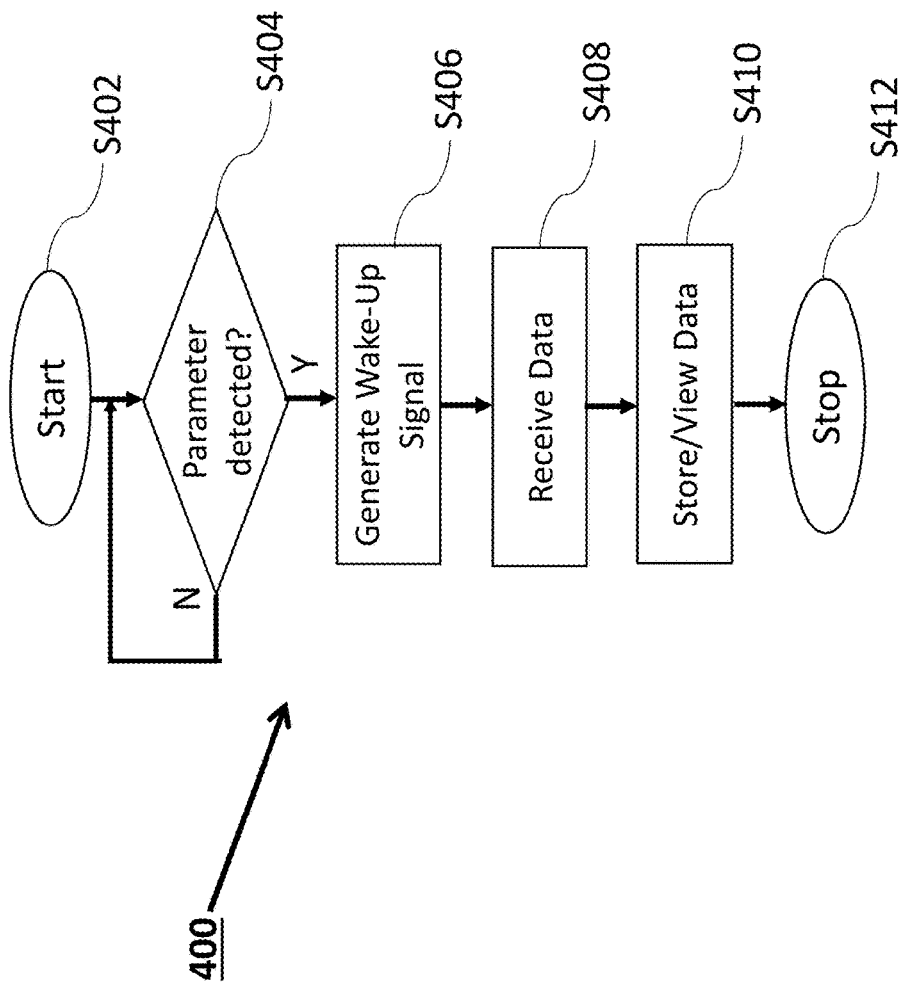
FIG. 4 illustrates an example method of detecting parameters of shoes and a golf club and communicating the detected parameters to an external device in accordance with aspects of the present invention.

FIG. 4 illustrates an example method 400 of detecting shoes and golf club parameters and communicating the detected parameters to an external device in accordance with aspects of the present invention.

Method 400 starts (S402) and it is determined if a parameter is detected (S404).

Figure 5:
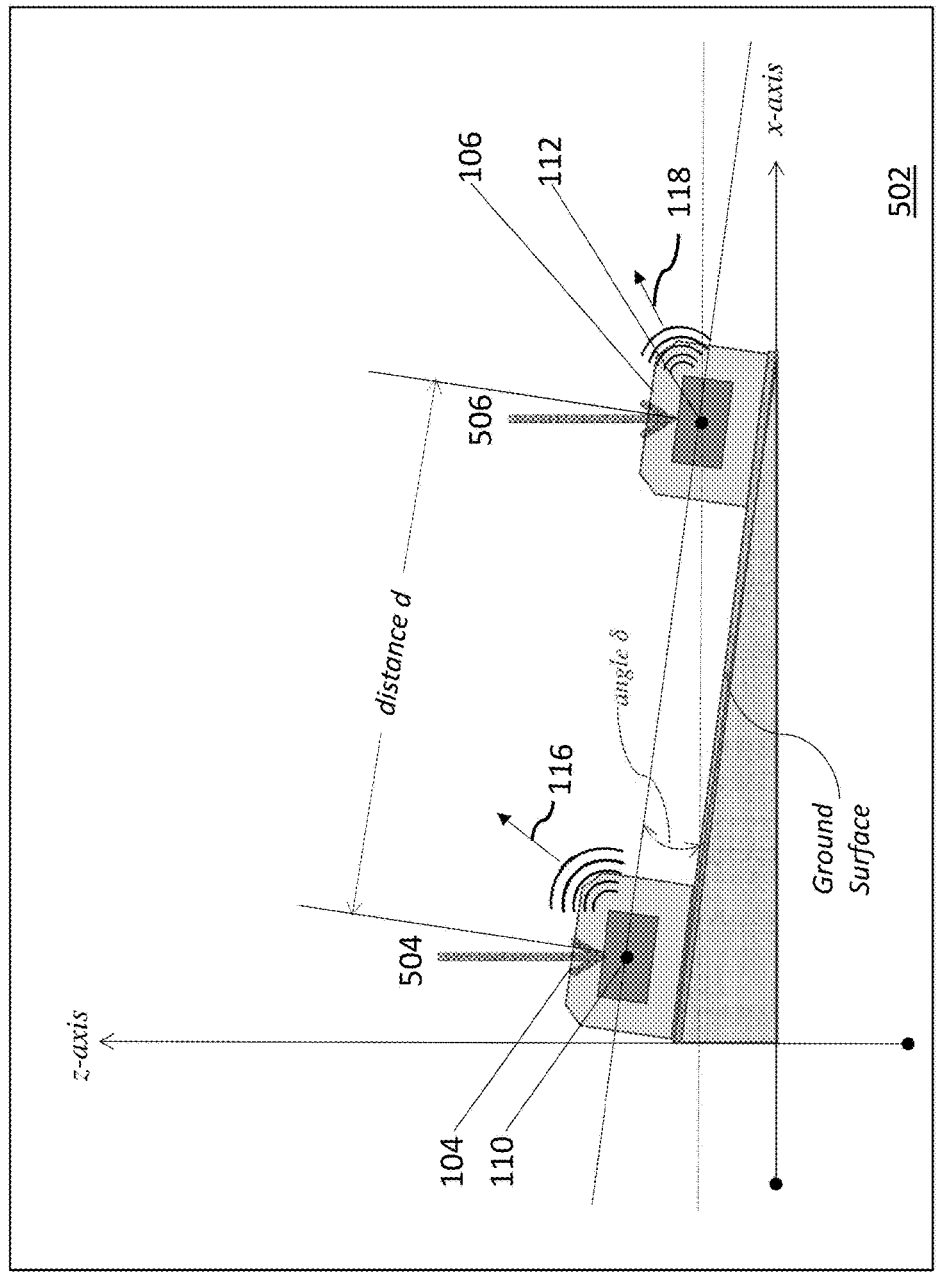
FIG. 5 illustrates the elevation view of shoes from behind the golfer.

An example of parameters that may be detected by shoes 104 and 106 will now be further described in FIG. 5.

FIG. 5 illustrates the elevation view of shoe 104 and shoe 106 from behind the golfer. Shoe 104 is higher in elevation than shoe 106, as if on a hillside.

As shown in the figure, the center of shoe parameter detector 110 is a distance d from the center of shoe parameter detector 112, and angle δ above the shoe parameter detector 112. in this example, shoe parameter detector 110 is able to detect pressure as applied by the user's left foot, which is represented by arrow 504, whereas shoe parameter detector 112 is able to detect pressure as applied by the user's right foot, and which is represented by arrow 506. It should be noted that this is merely a non-limiting example for purposes of discussion, wherein any number of parameters may be detected.

Figure 6:
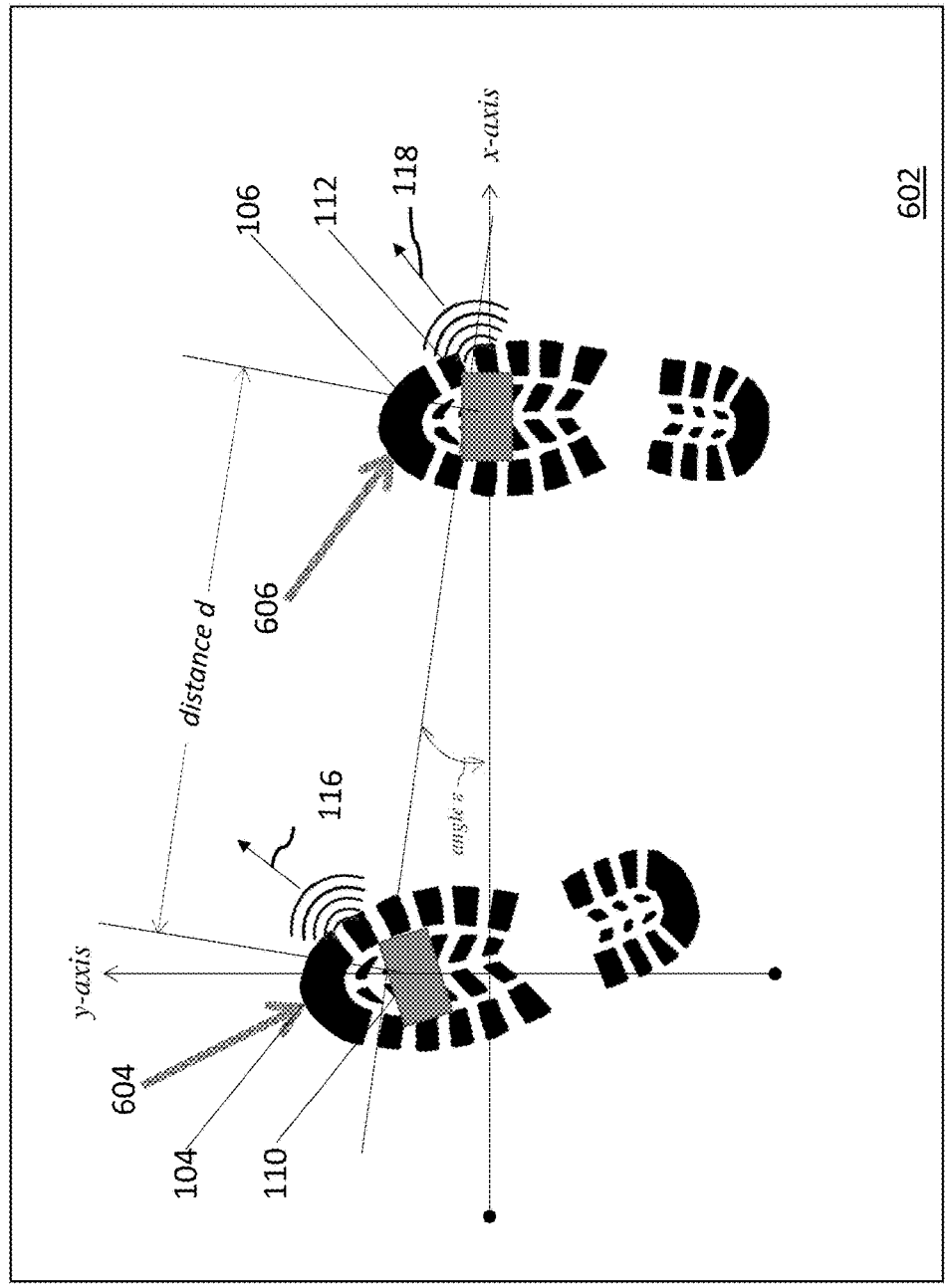
FIG. 6 illustrates the planar view of the shoes.

FIG. 6 illustrates the planar view of shoe 104, shoe 106, shoe parameter detector 110, and shoe parameter detector 112 from directly above the golfer. In this embodiment, shoe 104 is forward of the shoe 106 in planar view in the y direction.

Figure 7:
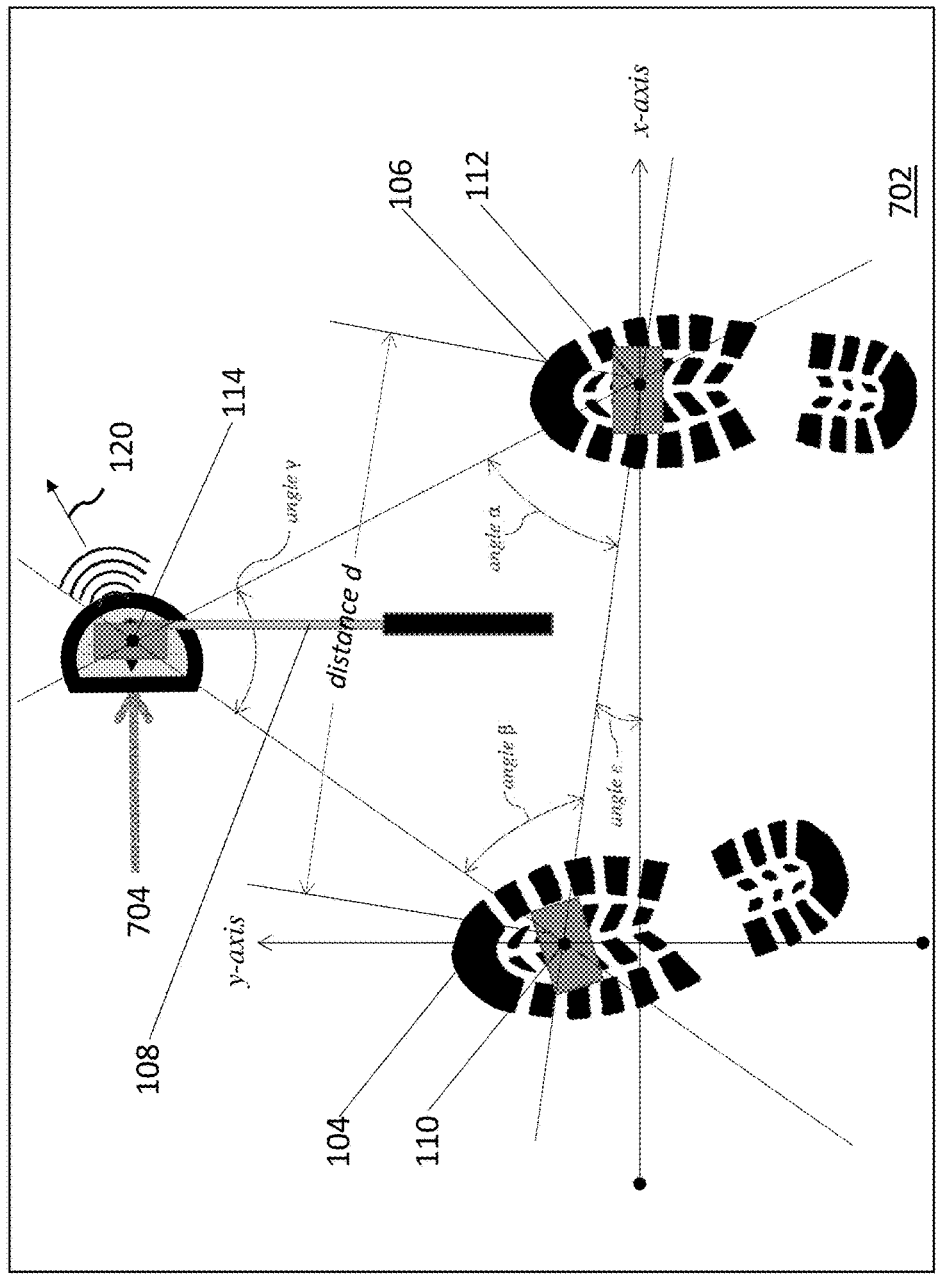
FIG. 7 illustrates the planar view of the shoes and a golf club.

As shown in FIG. 6, the center of shoe parameter detector 110 is separated from the center of shoe parameter detector 112 by an angle ε. For purposes of discussion, in this example, shoe parameter detector 110 is able to detect pressure as applied by the user's left foot, which is represented by arrow 604, whereas shoe parameter detector 112 is able to detect pressure as applied by the user's right foot, and which is represented by arrow 606. It should be noted that this is merely a non-limiting example for purposes of discussion, wherein any number of parameters may be detected. FIG. 7 will show similar relationships in the planar view including the golf club 108.

FIG. 7 illustrates the planar view of shoe 104, shoe 106, and golf club 108, shoe parameter detector 110, shoe parameter detector 112, and golf club parameter detector 114. Shoe 104 and golf club 108 are forward of shoe 106 in the y direction for illustrative purposes.

As shown in the figure, shoe parameter detector 110, shoe parameter detector 112, and golf club parameter detector 114 will always have three distances and three angles which can provide the position of each component, shoe parameter detector 110, shoe parameter detector 112, and golf club parameter detector 114 relative to one another. These distances and angles can provide geodetic locations relative to one another to determine components distance d, angle $\varepsilon$, angle $\alpha$, angle $\beta$, and angle $\gamma$. In this example, the vertical centerline of shoe parameter detector 110 is the y-axis and the horizontal centerline of shoe parameter detector 112 is the x-axis and all geodetic references are relative to this configuration. The distance d and all angles in this example are described as follows; distance d is from the centerline of detector 110 and 112; angle $\varepsilon$ is the angle from center and level of second shoe to center of first shoe; angle $\alpha$ is the angle between shoe parameter detector 110 and golf parameter detector 114; angle $\beta$ is the angle between shoe parameter detector 112 and golf parameter detector 114; and angle $\gamma$ is the angle between shoe parameter detector 110 and shoe parameter detector 112.

In this embodiment, a force applied to the head of golf club 108 is represented by an arrow 704. The force represented by arrow 704 is detected by golf club parameter detector 114. It should be noted that this is merely a non-limiting example for purposes of discussion, wherein any number of parameters may be detected.

In summary, in this example, as shown in FIG. 5: shoe parameter detector 110 is able to detect pressure from the user's left foot; and shoe parameter detector 112 is able to detect pressure from the user's right foot. Further, in this example, as shown in FIGS. 5-7: shoe parameter detector 110 is able to detect its relative position with respect to shoe parameter detector 112 and golf club parameter detector 114; shoe parameter detector 112 is able to detect its relative position with respect to shoe parameter detector 110 and golf club parameter detector 114; and golf club parameter detector 114 is able to detect its relative position with respect to shoe parameter detector 110 and shoe parameter detector 110. Still further, in this example, as shown in FIG. 7, golf club parameter detector 114 is able to detect force from the ball (not shown) as it is being hit.

Returning to FIG. 4, if a parameter is not detected (NO at S404), then method 400 continues until a parameter is detected (return to S404). If a parameter is detected (Y at S404), then a wake-up signal is generated (S406). For example, if any one of shoe parameter detector 110, shoe parameter detector 112 and golf club parameter detector 114 detect a parameter, a wake-up signal may be generated. This will be described in greater detail with reference to FIG. 8.

Figure 8:
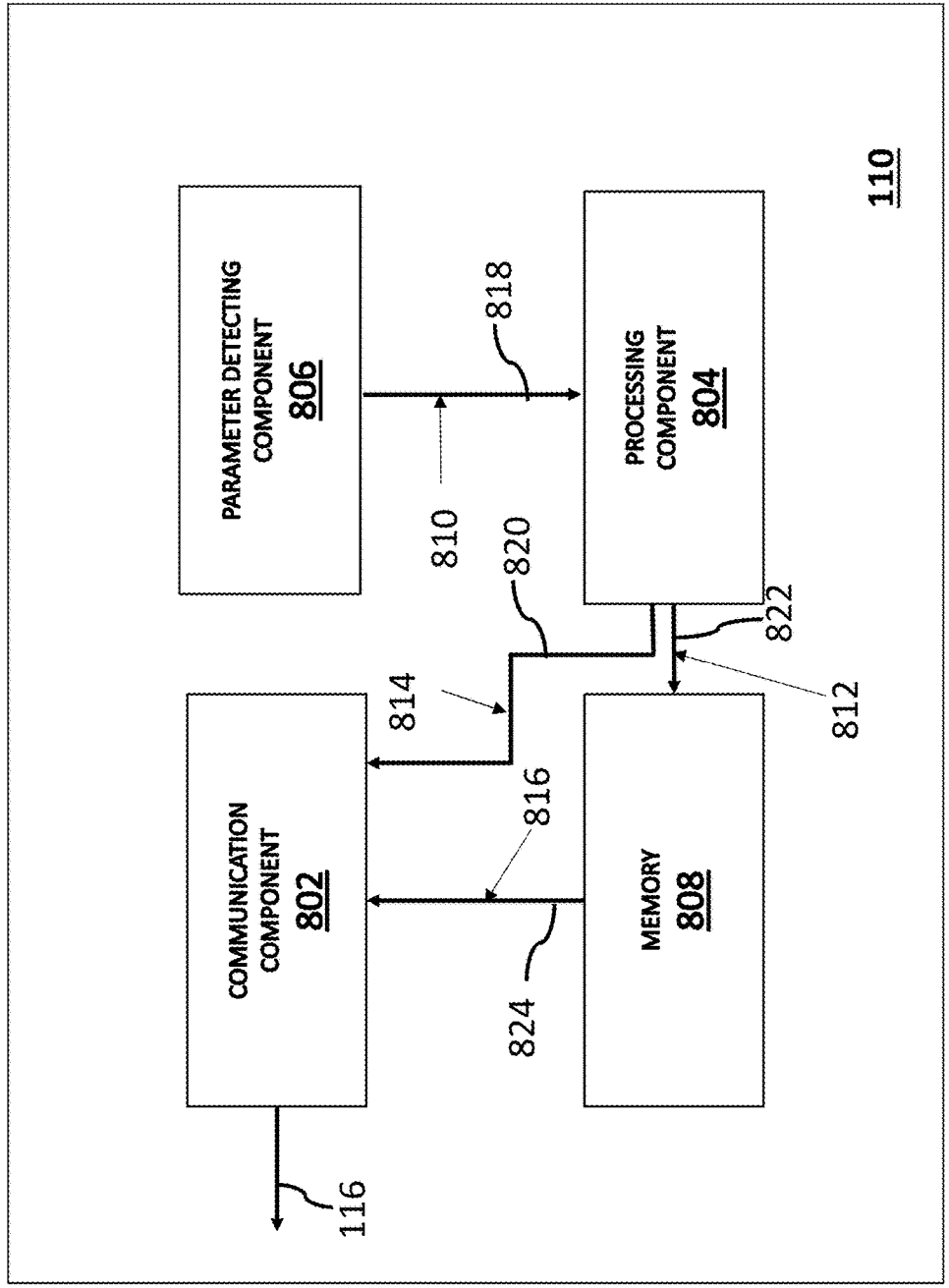
FIG. 8 illustrates the shoe parameter detector of FIG. 1.

FIG. 8 illustrates an exploded view of shoe parameter detector 110, which includes a communications component 802, a processing component 804, a parameter detecting component 806, a memory 808 and communication channels 810, 812, 814 and 816.

In this example, communications component 802, processing component 804, parameter detecting component 806, and memory 808 are illustrated as individual devices. However, in some embodiments, at least two of communications component 802, processing component 804, parameter detecting component 806 and memory 808 may be combined as a unitary device. Further, in some embodiments, at least one of communications component 802, processing component 804, parameter detecting component 806 and memory 808 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

Parameter detecting component 806 is arranged to communicate with processing component 804 via communication channel 810. Processing component 804 is additionally arranged to communicate with memory 808 via communication channel 812 and to communicate with communication component 802 via communication channel 814. Memory 808 is additionally arranged to communicate with communication component 802 via communication channel 816.

A shoe parameter may be detected by parameter detecting component 806. For purposes of explanation, let the detected shoe parameter be pressure as applied by the user's left foot (see arrow 504 of FIG. 5). Parameter detecting component 806 generates a pressure signal 818 associated with the detected pressure or change in pressure and sends pressure signal 818 to processing component 804 via communication channel 810. As other non-limiting examples, signals corresponding to orientation, position, and force, respectively, may be generated by parameter detecting component 806.

Processing component 804 may process the pressure signal to generate a wake-up signal 820. In some embodiments, any signal received from parameter detecting component 806 may be compared with a predetermined threshold to determine whether a wake-up signal 820 should be generated. For example, a certain pressure threshold may be established that would indicate that the user is actually standing in shoe 104. Such a threshold would eliminate wasted resources of generating a wake-up signal 820 when the shoe 104 is merely rested on a shelf after use. Other embodiments may use other detected parameters, other thresholds, or combinations thereof to determine whether a wake-up signal 820 may be generated.

Processing component 804 then sends wake-up signal 820 to communications component 802 via communications channel 814. Further, if wake-up signal 820 is generated, processing component 804 may send signal 822, which includes information related to the parameter that is detected by parameter detecting component 806, to memory 808 via communication channel 812. More particularly, information related to any parameters detected by parameter detecting component 806 may be sent to memory 808 for storage. For example, information related to position, elevation, orientation, pressure, force, velocity, acceleration, change in elevation, change in orientation, change in pressure, change in force, change in acceleration and combinations thereof of shoe 104 may be stored.

In some embodiments, memory 808 provides information associated with signal 822 to communication component 802 as signal 824. For example, memory 808 may provide information related to related to position, elevation, orientation, pressure, force, velocity, acceleration, change in elevation, change in orientation, change in pressure, change in force, change in acceleration and combinations thereof of shoe 104 as signal 824. In other embodiments, memory 808 may provide signal 824 in response to a request from controller 100 via communication component 802.

In a non-limiting example embodiment, communications component 802 then sends wake-up signal 820 and signal 824 to controller 100 as shoe parameter signal 116. In this manner, controller 100 will wake up and be provided with the parameter information detected by shoe parameter detector 110.

In another embodiment, communications component 802 first sends only wake-up signal 820 to controller 100 as shoe parameter signal 116 to wake up controller 100. Controller 100 may then provide a request for detected parameter information. Then, communications component 802 sends only signal 824 to controller 100 as shoe parameter signal 116.

For purposes of brevity, it should be noted that shoe parameter detector 112 and golf club parameter detector 114 may operate in a similar fashion to shoe parameter detector 110. However, in some embodiments, each of shoe parameter detector 112 and golf club parameter detector 114 may detect different parameters.

Any one of shoe parameter detector 110, shoe parameter detector 112 and golf club parameter detector 114 may wake up controller 100 with a respective wake-up signal.

Returning to FIG. 4, after a wake-up signal (or signals as the case may be) is generated (S406), the data is received (S408). This will be described in greater detail with reference to FIGS. 9-10.

Figure 9:
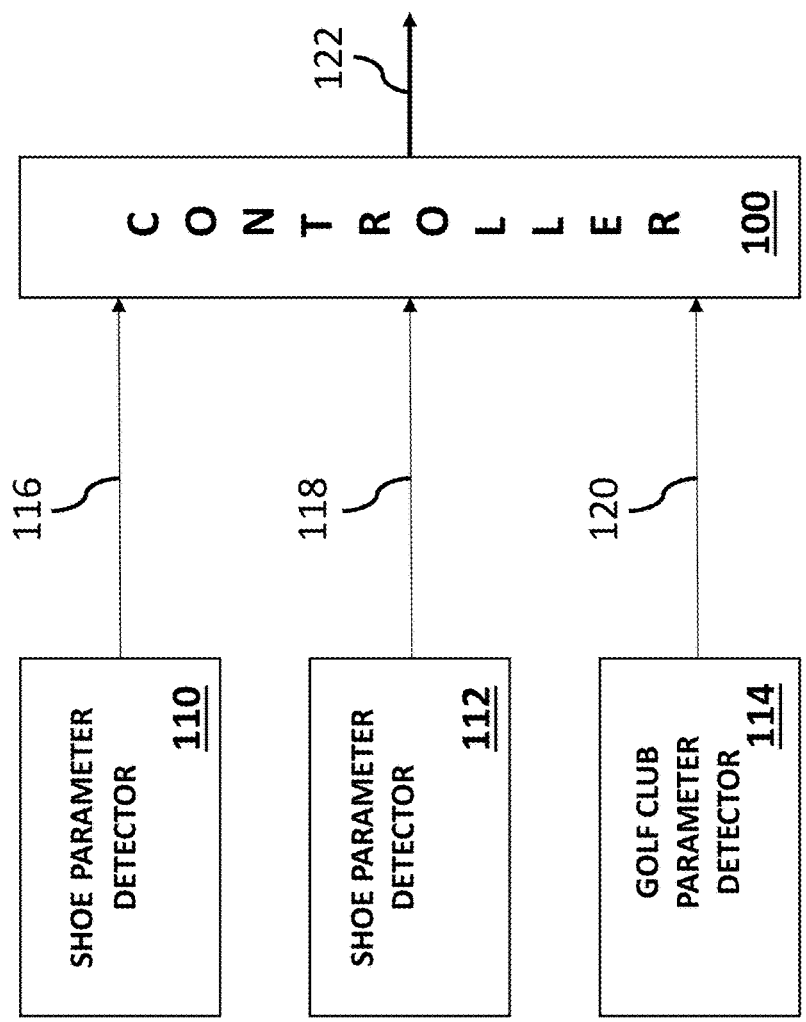
FIG. 9 illustrates a block diagram of a system with shoe detectors, a golf club detector, and a controller in accordance with aspects of the present invention.

FIG. 9 illustrates a block diagram of a system with shoe parameter detector 110, shoe parameter detector 112, golf club parameter detector 114, and controller 100 in accordance with aspects of the present invention.

In FIG. 9, shoe parameter detector 110 detects parameters and sends to controller 100 via shoe parameter signal 116. Shoe parameter detector 112 detects parameters and sends to controller 100 via shoe parameter signal 118. Golf club parameter detector 114 detects parameter and sends to controller 100 via golf club parameter signal 120. The controller 100 receives input signals 116, 118, and 120 and sends a performance signal 122, which is a composite of the parameter signals, to external devices, e.g., smartphones and computers. This will be described in greater detail with reference to FIG. 10.

Figure 10:
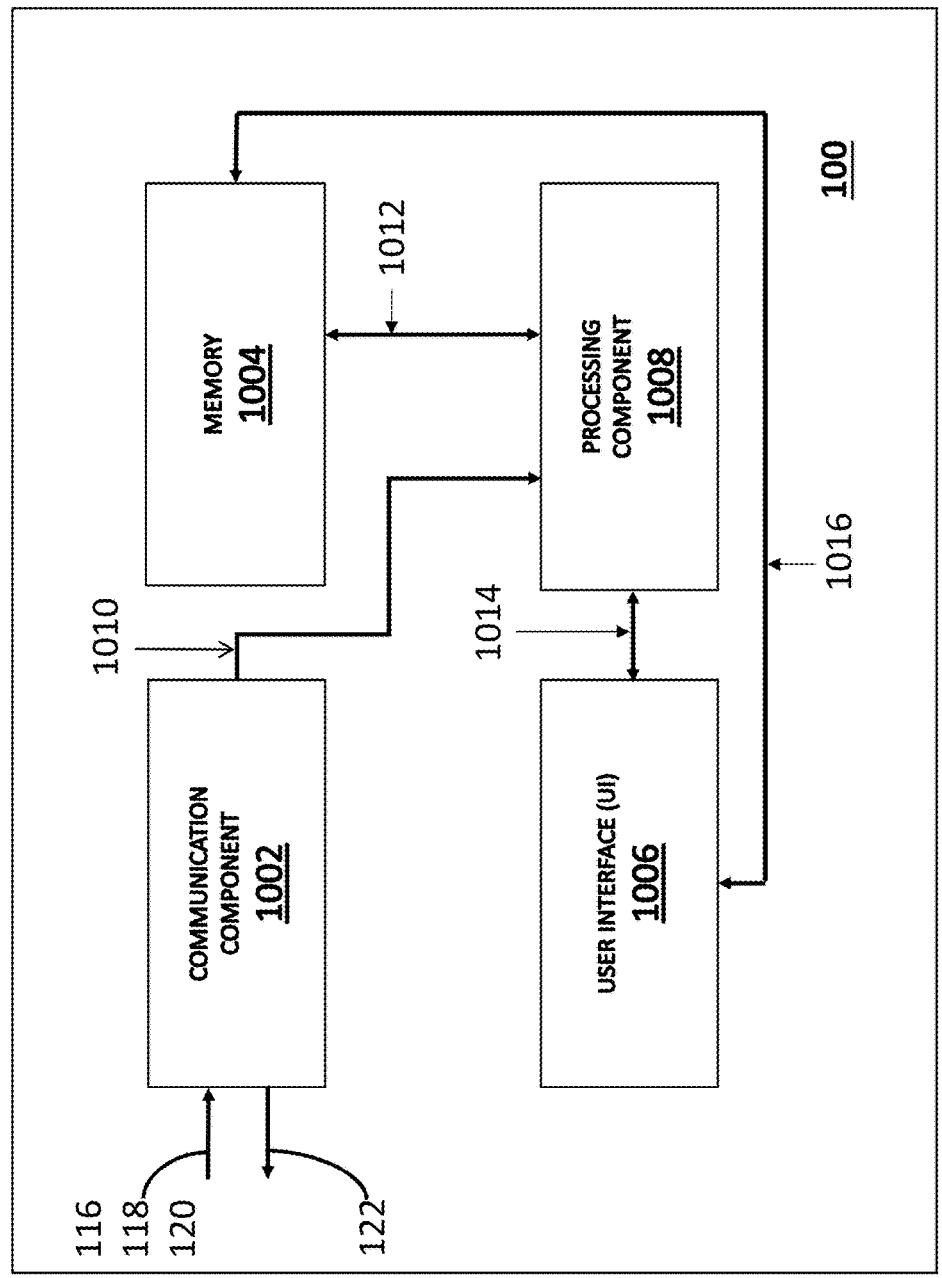
FIG. 10 illustrates a controller of the system of FIG. 1.

FIG. 10 illustrates an exploded view of controller 100, which includes a communications component 1002, a memory 1004, a user interface (UI) 1006, a processing component 1008 and communication channels 1010, 1012, 1014 and 1016.

In this example, communications component 1002, memory 1004, UI 1006 and processing component 1008 are illustrated as individual devices. However, in some embodiments, at least two of communications component 1002, memory 1004, UI 1006 and processing component 1008 may be combined as a unitary device. Further, in some embodiments, at least one of communications component 1002, memory 1004, UI 1006 and processing component 1008 may be implemented as a computer having tangible computer-readable media for carrying or having computer-executable instructions or data structures stored thereon.

Communication component 1002 is arranged to communicate with processing component 1008 via communication channel 1010. Processing component is additionally arranged to communicate with memory 1004 via communication channel 1012 and with UI 1006 via communication channel 1014. Memory 1004 is additionally arranged to communicate with UI 1006 via communication channel 1016.

As shown in the figure, communication component 1002 receives any of detected shoe parameter signals 116, 118, and golf club parameter signal 120 and sends them to processing component 1008. Processing component 1008 processes any of detected shoe parameter signals 116, 118, and golf club parameter signal 120 to generate performance signal 122. Non-limiting examples of types of processing include using the exact values of detected shoe parameter signals 116, 118, and golf club parameter signal 120 or some predetermined functional relationship between detected shoe parameter signals 116, 118, and golf club parameter signal 120.

Processing component outputs data associated with performance signal 122 to memory 1004 for storage. Further, processing component enables UI 1006 to access the data associated with performance signal 122. In this manner, UI 1006 enables user 102 to access data associated with performance signal 122 in real-time from processing component 1008 or at a later time from memory 1004. In other words, user 102 is able to view data associated with a golf swing as detected by shoes 104 and 106 and by golf club 108.

Communications component 1002 also receives performance signal 122 from processing component 1008 and may output performance signal 122 to any external device. In a non-limiting example, user 102 may receive performance signal 122 on a smartphone.

Returning to FIG. 4, after the data is received (S408), method 400 stores the data for real-time viewing or for viewing at a later time (S410) allowing accurate feedback for the golf swing. Real-time or later viewing via the GUI is available via the controller or at a later time via external device. After the data is stored and/or viewed, method 400 stops (S412).

The data obtained from the controller can be stored on a phone, computer, or any other GUI or storage device to be retrieved later to observe performance In some embodiments, parameters associated with the shoes and golf club may be detected in predetermined intervals, such as at the start of the back-swing, at the start of the forward swing and at the end of the follow through. In some embodiments, parameters associated with the shoes and golf club may be detected continuously throughout an entire swing.

Noting the swing, stance, force, position of shoes, etc . . . with good and bad shots can be used later to changed shoe position(s) and/or golf club head position/speed, etc., to emulate the swing associated with the good shots. Monitoring golf swing performance over a period of time allows the user to change or continue with the current training regiment depending on desired performance A video of the golf swing from a session on the driving range could be used in conjunction with the data obtained from the invention by a golf trainer that doesn't need to be present at the driving range to assist with improving the swing.

In summary, the above described embodiments of the invention relate to a system and method to improve a golf swing by recording and storing detected parameters from detectors detachably affixed to shoes and golf club head for later viewing by the user. The parameter detectors disposed at the shoes and golf club head provide numerous detected parameters and send these parameters to the controller, which can send via signals to external devices for viewing, comparison, etc. Incorporating changes to shoe(s) and golf club head using the following non-limiting parameters: position, orientation, pressure, force, velocity, acceleration, change in orientation, change in pressure, change in force, change in acceleration and combinations thereof, has the potential to improve golf swing performance The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A system for use by a user and for use with a golf club, the system comprising:
    a first shoe for being worn by the user and comprising at least a first sensor configured to detect a first shoe parameter;
    a second shoe for being worn by the user and comprising at least a second sensor configured to detect a second shoe parameter;
    a golf club sensor detachably fastened to the golf club, the sensor configured to detect a position parameter of a ball-striking surface of a head of the golf club relative to at least one of the first shoe and the second shoe;
    a remote controller apparatus configured to:
    receive the first shoe parameter, the second shoe parameter, and the position parameter from the respective first shoe, second shoe and golf club sensors via a wireless communication protocol;
    generate a performance signal comprising a composite of the first shoe parameter, the second shoe parameter, and the position parameter; and
    output the performance signal to an external display apparatus; and
    an external display apparatus configured to receive the performance signal from the remote controller apparatus via a wireless communication protocol and to display the performance signal to the user via a display thereof.

2. The system of claim 1, wherein the first shoe parameter comprises an orientation of the first shoe, and wherein the second shoe parameter comprises an orientation of the second shoe.

3. The system of claim 1, wherein at least one of the first and second shoe parameters comprises a position of the first shoe relative to the second shoe.

4. The system of claim 3, wherein the golf club sensor is configured to detect the position of the ballstriking surface at a first time, a second position of the ball-striking surface at a second time, and a third position of the ball-striking surface at a third time.

5. The system of claim 1, wherein the first shoe parameter comprises at least one of: pressure associated with the first shoe, and force associated with the first shoe, and wherein the second shoe parameter comprises at least one of: pressure associated with the second shoe, and force associated with the second shoe.

6. The system of claim 1, wherein the first shoe parameter, the second shoe parameter, and the position parameter are collected over a time period comprising at least one of:
    an entire time period throughout which the user swings the golf club;
    a portion of the entire time period throughout which the user swings the golf club which encompasses a back swing;
    a portion of the entire time period throughout which the user swings the golf club which encompasses a forward swing; and
    entire time period throughout which the user swings the golf club which encompasses a follow-through.

7. The system of claim 1, wherein the performance signal comprises a functional relationship between one or more of: the first shoe parameter, the second shoe parameter, and the position parameter.

8. A method comprising:
    receiving at a computer apparatus from one or more shoe parameter sensors disposed at one or more shoes worn by a user, shoe parameter data, the shoe parameter data comprising orientation, acceleration, and position of the one or more shoes throughout the duration of a swing of a golf club by the user and the orientation data comprising an orientation of a first shoe and an orientation of a second shoe relative one another;
    receiving, at the computer apparatus golf club data from a golf club parameter sensor detachably fastened to the golf club, the golf club data comprising acceleration, force, and velocity of the golf club throughout the duration of the swing of the golf club by the user;
    processing the golf club data and the shoe parameter data at the computer apparatus to generate a performance signal; and
    outputting the performance signal to a mobile apparatus via wireless communication therewith for display to the user.

9. The method of claim 8, wherein the position data comprises a position of the first shoe relative to the second shoe.

10. The method of claim 9, wherein the golf club data further comprises a position of a ball-striking surface of a head of the golf club about a shaft of the golf club relative to a position of at least one shoe.

11. The method of claim 8, wherein the shoe parameter data further comprises at least one of: pressure associated with the one or more shoes, and force associated with the one or more shoes.

12. The method of claim 8, wherein the performance signal comprises composite of the shoe parameter data and the golf club data.

13. The method of claim 8, wherein the computer apparatus comprises the mobile apparatus which is configured to display the performance signal.

* * * * *